United States Patent
Herrick et al.

(10) Patent No.: US 9,596,857 B2
(45) Date of Patent: *Mar. 21, 2017

(54) INSECTICIDAL AND MITICIDAL MIXTURES OF BIFENTHRIN AND CYANO-PYRETHROIDS

(71) Applicant: FMC Corporation, Philadelphia, PA (US)

(72) Inventors: Robert M. Herrick, Hamilton, NJ (US); Mark Walmsley, Morristown, NJ (US); Charles A. Staetz, Nevada City, CA (US); Hui S. Yang, Plainsboro, NJ (US); D. Craig Heim, Westmont, NJ (US); Hylsa Garcia, Ponce, PR (US); Nancy Hilton, Philadelphia, PA (US)

(73) Assignee: FMC Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/662,480

(22) Filed: Mar. 19, 2015

(65) Prior Publication Data

US 2015/0189874 A1    Jul. 9, 2015

Related U.S. Application Data

(63) Continuation of application No. 12/158,487, filed as application No. PCT/US2006/049062 on Dec. 21, 2006.

(60) Provisional application No. 60/752,979, filed on Dec. 22, 2005.

(51) Int. Cl.
| | |
|---|---|
| *A01N 53/06* | (2006.01) |
| *A01N 37/34* | (2006.01) |
| *A01P 7/04* | (2006.01) |
| *A01N 53/00* | (2006.01) |
| *A01N 37/10* | (2006.01) |

(52) U.S. Cl.
CPC ............. *A01N 53/00* (2013.01); *A01N 37/10* (2013.01); *A01N 37/34* (2013.01)

(58) Field of Classification Search
CPC .... A01N 53/00; A01N 2300/00; A01N 25/02; A01N 25/04; A01N 37/10; A01N 37/34
USPC .................................................. 514/521, 531
See application file for complete search history.

(56) References Cited

U.S. PATENT DOCUMENTS

| | | | |
|---|---|---|---|
| 3,899,586 A | | 8/1975 | Okuno |
| 4,997,970 A | * | 3/1991 | Ager, Jr. ...................... 558/354 |
| 5,028,731 A | | 7/1991 | Glenn |
| 5,164,411 A | | 11/1992 | Baum |
| 6,713,077 B1 | | 3/2004 | Kohn |
| 6,794,576 B1 | | 9/2004 | Justason et al. |
| 6,825,227 B2 | | 11/2004 | Valdez et al. |
| 2005/0049146 A1 | | 3/2005 | Chiarello et al. |
| 2005/0215433 A1 | | 9/2005 | Benitez et al. |

FOREIGN PATENT DOCUMENTS

| | | |
|---|---|---|
| WO | 9740692 A1 | 11/1997 |
| WO | 03053345 A2 | 7/2003 |
| WO | WO 03053345 A2 * | 7/2003 |

OTHER PUBLICATIONS

Alan Wood Database [online]. Copyright © 1995-2010 [retrieved on Dec. 14, 2010]. Retrieved from the Internet:www.alanwood.net/pesticides/zeta-cypermeth rin.html>.*
Zeta-Cypermethrin Data Sheet, [online] www.alanwood.net/pesiticides/zeta-cypermethrin.html Dec. 19, 2010, 2 pages.

* cited by examiner

*Primary Examiner* — Janet Epps-Smith
*Assistant Examiner* — Courtney Brown
(74) *Attorney, Agent, or Firm* — FMC Corporation

(57) ABSTRACT

The present invention is directed to a novel insecticidal composition comprising bifenthrin and a cyano-pyrethroid which exhibit an unexpected increase in insecticidal activity as compared to the insecticidal activity of the individual components. The present invention is also directed to a novel insecticidal composition comprising bifenthrin and a cyano-pyrethroid in admixture with at least one agriculturally acceptable extender or adjuvant.

11 Claims, No Drawings

INSECTICIDAL AND MITICIDAL MIXTURES OF BIFENTHRIN AND CYANO-PYRETHROIDS

This application claims the benefit of U.S. Provisional Application No. 60/752,979 filed Dec. 22, 2005.

FIELD OF THE INVENTION

The present invention relates to the field of insecticides. In particular, the invention provides novel insecticidal compositions comprising bifenthrin and a cyano-pyrethroid that exhibit unexpected insecticidal activity.

BACKGROUND OF THE INVENTION

It is well known that insects in general can cause significant damage, not only to crops grown in agriculture, but also, for example, to structures and turf where the damage is caused by soil-borne insects, such as termites and white grubs. Such damage may result in the loss of millions of dollars of value associated with a given crop, turf or structures. Insecticides and acaricides are useful for controlling insects and acarids which may otherwise cause significant damage to crops such as wheat, corn, soybeans, potatoes, and cotton to name a few. For crop protection, it is desirable to use effective chemical insecticides and acaricides which can control the insects and acarids without damaging the crops, and which have no deleterious effects to mammals and other living organisms.

For commercial agricultural use it would be of benefit to combine insecticides that have somewhat different spectrums of activity and residual effectiveness in order to benefit from each of the individual insecticidal properties. Mixtures containing two or more insecticide compositions have been practiced in the art in order to benefit from the insecticidal properties of the individual components. For example, U.S. Pat. No. 3,899,586 discloses an insecticidal and/or acaricidal composition obtained by mixing N-(3,4,5, 6-tetrahydrophthalimide)-methyl chrysanthemate with 5-(2-propynyl)furfuryl 3-(2,2-dichlorovinyl)-2,2-dimethylcyclopropanecarboxylate.

SUMMARY OF THE INVENTION

In accordance with the present invention, it has now been found that a novel insecticidal composition comprising bifenthrin and a cyano-pyrethroid exhibit an unexpected increase in insecticidal activity as compared to the insecticidal activity of the individual components. The present invention is also directed to a novel insecticidal composition comprising bifenthrin and a cyano-pyrethroid in admixture with at least one agriculturally acceptable extender or adjuvant.

DETAILED DESCRIPTION OF THE INVENTION

In accordance with the present invention, it has now been found that a novel insecticidal composition comprising bifenthrin and a cyano-pyrethroid exhibit an unexpected increase in insecticidal activity as compared to the insecticidal activity of the individual components. The present invention is also directed to a novel insecticidal composition comprising bifenthrin and a cyano-pyrethroid in admixture with at least one agriculturally acceptable extender or adjuvant.

Synthetic pyrethroids which contain a cyano group (cyano-pyrethroids) are very potent insecticides, for example, zeta-cypermethrin is a potent and quick acting insecticide, which controls a broad spectrum of chewing, sucking and flying insects. In addition to controlling chewing, sucking and flying insects, the pyrethroid bifenthrin is also active against a number of key mite pests and exhibits a longer residual activity than zeta-cypermethrin. It has now been discovered that by combining these two potent insecticides, an unexpected increase in insecticidal activity is observed in certain insect species. In addition to being very potent and quick acting insecticides, cyano-pyrethroids often cause mammalian skin irritation. By using a mixture which contains less bifenthrin and less cyano-pyrethroid to achieve insecticidal activity superior to either insecticidal compound alone, an ecological and mammalian safety benefit is realized.

Specifically, one aspect of the present invention is directed to an insecticidal composition comprising bifenthrin and a cyano-pyrethroid.

Another aspect of the present invention is directed to an insecticidal composition comprising bifenthrin and a cyano-pyrethroid, in admixture with at least one agriculturally acceptable extender or adjuvant.

Another aspect of the present invention relates to methods of controlling insects by applying an insecticidally effective amount of a composition as set forth above to a locus of crops such as, without limitation, cereals, cotton, vegetables, and fruits, or other areas where insects are present or are expected to be present.

The term "bifenthrin" means 2-methylbiphenyl-3-ylmethyl (Z)-(1RS)-cis-3-(2-chloro-3,3,3-trifluoroprop-1-enyl)-2,2-dimethyl cyclopropanecarboxylate.

The term "cyano-pyrethroid" means an insecticidal pyrethroid that contains a cyano group. The cyano-pyrethroid is selected from the group consisting of, but not limited to:

acrinathrin which is (S)-α-cyano-3-phenoxybenzyl (Z)-(1R)-cis-2,2-dimethyl-3-[2-(2,2,2-trifluoro-1-trifluoromethylethoxycarbonyl)vinyl]cyclopropanecarboxylate, cycloprothrin which is (RS)-α-cyano-3-phenoxybenzyl (RS)-2,2-dichloro-1-(4-ethoxyphenyl)cyclopropanecarboxylate], deltamethrin [(S)-α-cyano-3-phenoxybenzyl (1R)-cis-3-(2,2-dibromovinyl)-2,2-dimethylcyclopropanecarboxylate, tralomethrin which is (S)-α-cyano-3-phenoxybenzyl(1R)-cis-2,2-dimethyl-3-[(RS)-1,2,2,2-tetrabromoethyl]cyclopropanecarboxylate, fenvalerate which is (RS)-α-cyano-3-phenoxybenzyl (RS)-2-(4-chlorophenyl)-3-methylbutyrate, cyfluthrin which is (RS)-α-cyano-4-fluoro-3-phenoxybenzyl (1RS)-cis-trans-3-(2,2-dichlorovinyl)-2,2-dimethylcyclopropanecarboxylate, beta-cyfluthrin which is a reaction mixture comprising the enantiomeric pair (R)-α-cyano-4-fluoro-3-phenoxybenzyl (1S)-cis-3-(2,2-dichlorovinyl)-2,2-dimethylcyclopropanecarboxylate and (S)-α-cyano-4-fluoro-3-phenoxybenzyl (1R)-cis-3-(2,2-dichlorovinyl)-2,2-dimethylcyclopropanecarboxylate in ratio 1:2 with the enantiomeric pair (R)-α-cyano-4-fluoro-3-phenoxybenzyl (1S)-trans-3-(2,2-dichlorovinyl)-2,2-dimethylcyclopropanecarboxylate and (S)-α-cyano-4-fluoro-3-phenoxybenzyl (1R)-trans-3-(2,2-dichlorovinyl)-2,2-dimethylcyclopropanecarboxylate, flucythrinate which is (RS)-α-cyano-3-phenoxybenzyl (S)-2-(4-difluoromethoxyphenyl)-3-methylbutyrate, alpha-cypermethrin which is a racemate comprising (S)-α-cyano-3-phenoxybenzyl (1R)-cis-3-(2,2-dichlorovinyl)-2,2-dimethylcyclopropanecarboxylate and (R)-α-cyano-3- phenoxybenzyl (1S)-cis-3-(2,2-dichlorovinyl)-2,2-dimethylcyclopropanecarboxylate, beta-cypermethrin which is a reaction mixture comprising two enantiomeric pairs in a ratio of about 2:3 (S)-α-cyano-3-phenoxybenzyl (1R)-cis-3-(2,2-dichlorovinyl)-2,2-dimethylcyclopropanecarboxylate and (R)-α-cyano-3-phenoxybenzyl (1S)-cis-3-(2,2-dichlorovinyl)-2,2-dimethylcyclopropanecarboxylate with (S)-α-cyano-3-phenoxybenzyl (1R)-trans-3-(2,2-dichlorovinyl)-2,2-dimethylcyclopropanecarboxylate and (R)-α-cyano-3-phenoxybenzyl (1S)-trans-3-(2,2-dichlorovinyl)-2,2-dimethylcyclopropanecarboxylate, theta-cypermethrin which is a 1:1 mixture of the enantiomers (R)-α-cyano-3-phenoxybenzyl (1S)-trans-3-(2,2-dichlorovinyl)-2,2-dimethylcyclopropanecarboxylate and (S)-α-cyano-3-phenoxybenzyl (1R)-trans-3-(2,2-dichlorovinyl)-2,2-dimethylcyclopropanecarboxylate, zeta-cypermethrin which is (R,S)-α-cyano-3-phenoxybenzyl-(1RS)-cis-trans-3-(2,2-dichlorovinyl)-2,2-dimethylcyclopropanecarboxylate which has been enriched in the 1R-cis-S and 1R-trans-S isomers, cyphenothrin which is (R,S)-α-cyano-3-phenoxybenzyl-(1R)-cis-trans-2,2-dimethyl-3-(2-methylprop-1-enyl)cyclopropanecarboxylate, cyhalothrin which is (R,S)-α-cyano-3-phenoxybenzyl-(Z)-(1RS)-cis-3-(2-chloro-3,3,3-trifluoropropenyl)-2,2-dimethylcyclopropanecarboxylate, lambda-cyhalothrin which is a reaction product comprising equal quantities of (S)-α-cyano-3-phenoxybenzyl-(Z)-(1R)-cis-3-(2-chloro-3,3,3-trifluoropropenyl)-2,2-dimethylcyclopropanecarboxylate and (R)-α-cyano-3-phenoxybenzyl-(Z)-(1S)-cis-3-(2-chloro-3,3,3-trifluoropropenyl)-2,2-dimethylcyclopropanecarboxylate, esfenvalerate which is (S)-α-cyano-3-phenoxybenzyl (S)-2-(4-chlorophenyl)-3-methylbutyrate, fluvalinate which is (RS)-α-cyano-3-phenoxybenzyl N-(2-chloro-α,α,α-trifluoro-p-tolyl)-DL-valinate, and fenpropathrin which is (RS)-α-cyano-3-phenoxybenzyl 2,2,3,3-tetramethylcyclopropanecarboxylate.

A particular form of zeta-cypermethrin is (R,S)-α-cyano-3-phenoxybenzyl-(1RS)-cis-trans-3-(2,2-dichlorovinyl)-2,2-dimethylcyclopropanecarboxylate which has been enriched in the 1R-cis-S and 1R-trans-S isomers by the processes disclosed in patents U.S. Pat. No. 5,164,411, U.S. Pat. No. 5,028,731 and U.S. Pat. No. 4,997,970. A most preferred form of zeta-cypermethrin is the isomer mixture prepared by the process disclosed in U.S. Pat. No. 4,997,970 starting with a 55/45 cis/trans mixture of cypermethrin with a catalytic amount of tricaprylylammonium chloride (Aliquat® 336, Aldrich Chemical Co.) and sodium carbonate in n-heptane. This process and subsequent isolation procedure produces zeta-cypermethrin containing a small amount, usually 0.6% to 1.3%, of the catalyst.

The ratio of bifenthrin active ingredient (AI) to cyano-pyrethroid AI may be from 1/99 to 99/1. Preferably the ratio of bifenthrin AI to cyano-pyrethroid AI is from 1/4 to 4/1. More preferably the ratio is from 1/3 to 3/1.

The present composition is effective against various insect pests and/or acarina pests. Insect pests and acarina pests to which the present composition can be applied are: Homoptera, which includes, for example, aphids, leafhoppers, cicadas, whiteflies, and mealybugs; Lepidoptera, which includes, for example, butterflies, moths and skippers; Coleoptera, which includes, for example, beetles and weevils; and Acarina, which includes, for example, mites and ticks.

The term "ambient temperature" as utilized herein shall generally mean any suitable temperature found in a laboratory or other working quarter, and is generally not below about 15° C. nor above about 30° C.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isophorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations and concentrated aqueous emulsion formulations (EWs) are similar to ECs, except that the active ingredient is suspended in a liquid carrier, generally water. Flowables, like ECs, may include one or more surfactants, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

Insecticide formulations may further comprise additional components such as an anti-freeze agent, an anti-foam agent and/or a biocide.

The compositions of the present invention are further illustrated by the examples below. The examples serve only to illustrate the invention and should not be interpreted as limiting since further modifications of the disclosed invention will be apparent to those skilled in the art. All such modifications are deemed to be within the scope of the invention as defined in the claims.

Example 1

This example illustrates one protocol for the preparation of a 2/1 ratio of bifenthrin to zeta-cypermethrin emulsifiable concentrate formulation To 42.32 grams of Aromatic 200 ND (available from ExxonMobile Chemicals) was added 8.34 grams of melted bifenthrin (95.9% active ingredient) and 11.11 grams of zeta-cypermethrin (36% active ingredient, prepared by the process disclosed in U.S. Pat. No. 4,997,970). The mixture was stirred at ambient temperature with a mechanical stirrer until a homogenous solution formed, at which time 2.52 grams of a branched dodecylbenzene sulfonate salt (Agnique ABS 70AE, available from Cognis Corporation), 0.28 gram of polyethylene glycol monooleate (Agnique PEG 400MO, available from Cognis Corporation) 0.84 gram of ethoxylated castor oil (Agnique CSO-36, available from Cognis Corporation), 1.96 grams ethoxylated castor oil (Agnique CSO-25, available from Cognis Corporation), 20.00 grams of severely solvent refined light and heavy paraffinic petroleum oil (Sunspray 6N, available from Sunoco, Inc.) and 0.08 gram of acetic acid were added. Upon completion of the addition, the agitation was continued for 10 minutes to obtain a yellowish homogeneous solution.

Candidate insecticide compositions were evaluated for activity in foliar evaluations against tobacco budworm (*Heliothis virescens* [Fabricius]), Colorado potato beetle (*Leptinotarsa decemlineata* [Say]), corn earworm (*Helicoverpa zea* [Boddie]), cotton aphid (*Aphis gossypii* [Glover]) and twospotted spider mite (*Tetranychus urticae* [Koch]). Each test included controls in which the formulation or test solution minus the active ingredients were applied.

In tests against tobacco budworm, the first true leaves of 7 to 10 day-old cotton plants (*Gossypium hirsutium*) were dipped into the test solutions of the test formulations to provide application rates as high as 10 ppm of the active ingredients, bifenthrin and zeta-cypermethrin (prepared by the process disclosed in U.S. Pat. No. 4,997,970). The test formulations were dissolved in distilled water containing 10% acetone and 0.25% of a non-ionic detergent [an octylphenolpoly(ethyleneglycolether)$_x$, available from Roche Applied Science as Triton X-100] to the proper concentrations. The treated plants were transferred to a hood where they were kept until the leaves had dried.

Each leaf was placed into a separate (100×20 mm) plastic Petri dish, containing a water-moistened filter paper. Five second-instar (7 day-old) tobacco budworms were placed into each Petri dish, taking care not to cause injury. The plastic lids were placed on each of the dishes, which were then held for 72 hours at 25° C., 50% relative humidity with a photo-period of 12 hours light and 12 hours dark. At the end of the 72 hour exposure period, the dishes were opened, and the numbers of dead and live insects were counted. Insects were classified as "dead" if they failed to rapidly right themselves when turned over. Using the insect counts, the activity of the test chemical was expressed in percent control. Percent control is derived from the total number of dead insects (TD) compared to the total number of insects (TI) in the test:

$$\%\ \text{Control} = \frac{TD}{TI} \times 100.$$

In tests against adult Colorado potato beetle, the leaves of 6-8 inch tall tomato plants (*Lycopersicon lycoper*) were dipped into the test solutions of the test formulations to provide application rates as high as 1000 ppm of the active ingredients. The test formulations were dissolved in distilled water containing 10% acetone and 0.25% of a non-ionic detergent [an octylphenolpoly(ethyleneglycolether)$_x$, available from Roche Applied Science as Triton X-100] to the proper concentrations. The treated plants were transferred to a hood where they were kept until the leaves had dried. For tests in which the active ingredients were not formulated, i.e. the technical active ingredient was used; a stock solution of the test compound was made. For example, a 100 ppm stock solution may be made by dissolving 4 milligrams of the test compound in 4 mL of acetone and adding the solution to 36 mL of an aqueous Triton X-100 solution (one drop of Triton X-100 dissolved in 100 mL of distilled water). Further dilutions can be made by adding distilled water containing 10% acetone and 0.25% of Triton X-100.

The treated tomato plants were removed from their pots by cutting the stems just above the soil line. Each excised plant was placed into an individual 8-ounce paper cup. Ten adult Colorado potato beetles were placed into each paper cup, taking care not to cause injury. An opaque plastic lid was placed on each cup, for a 72 hour exposure period and held at 25° C., 50% relative humidity with a photo-period of 12 hours light and 12 hours dark. At the end of the 72 hour exposure period, the cups were opened, and the numbers of dead and live insects were counted. Using the insect counts, the activity of the test chemical was expressed in percent control. Percent control is derived from the total number of dead insects (TD) compared to the total number of insects (TI) in the test:

$$\% \text{ Control} = \frac{TD}{TI} \times 100.$$

In tests against corn earworm, one inch diameter leaf discs cut from cotton plant leaves (*Gossypium hirsutum*) were dipped into the test solutions of the test formulations to provide application rates as high as 1000 ppm of the active ingredients. The test formulations were dissolved in distilled water containing 10% acetone and 0.25% of a non-ionic detergent [an octylphenolpoly(ethyleneglycolether)$_x$, available from Roche Applied Science as Triton X-100] to the proper concentrations. Cotton wicks, 0.5 inch diameter by 2 inches long, were soaked with distilled water and placed into the wells of a 32 well rearing tray (available as Rearing Tray Bio-Fit 32, from C-D International, Pittman, N.J.), one wick per well. Treated leaf discs were placed on top of the cotton wicks, one leaf disc per wick, and the rearing tray was transferred to a hood where they were kept until the leaf discs had dried. Each disc was infested with 1 late second to early third instar corn earworm, replicated sixteen times per rate of application, and a lid was placed on the rearing tray. The rearing trays were held in a growth chamber for 96 hours at 25° C., 50% relative humidity and a photoperiod of 12 hours light/12 hours dark. For tests in which the active ingredients were not formulated, i.e. the technical active ingredient was used; a stock solution of the test compound was made. For example, a 100 ppm stock solution may be made by dissolving 4 milligrams of the test compound in 4 mL of acetone and adding the solution to 36 mL of an aqueous Triton X-100 solution (one drop of Triton X-100 dissolved in 100 mL of distilled water). Further dilutions can be made by adding distilled water containing 10% acetone and 0.25% of Triton X-100.

At the end of the 96 hour exposure period, the rearing tray was opened, and the numbers of dead and live insects were counted. Insects were classified as "dead" if they failed to show movement when probed. Using the insect counts, the activity of the test chemical was expressed in percent control. Percent control is derived from the total number of dead insects (TD) compared to the total number of insects (TI) in the test:

$$\% \text{ Control} = \frac{TD}{TI} \times 100.$$

In tests against cotton aphid, the leaves of 6 to 8 inch tall tomato plants (*Lycopersicon lycoper*) were infested with about 50 cotton aphids by placing leaf cuttings from a cotton aphid colony host tomato plant. After about 12 hours the newly infested tomato leaves were dipped into the test solutions of the test formulations to provide application rates as high as 1000 ppm of the active ingredients. The test formulations were dissolved in, and diluted as necessary, with distilled water containing 10% acetone and 0.25% of a non-ionic detergent [an octylphenolpoly(ethyleneglycolether)$_x$, available from Roche Applied Science as Triton X-100] to the proper concentrations. After treatment, a square of parafilm was placed around the stem of each test plant, covering the soil of each pot in order to catch dead aphids that fall from the leaves. The treated plants were transferred to a hood where they were kept until the leaves had dried. Once dry, the potted plants were placed into a tray containing at least one inch of water. The plants were spaced far enough apart to prevent the aphids from moving between plants. The trays were held in a growth chamber for 72 hours at 25° C., 50% relative humidity and a photoperiod of 14 hours light/10 hours dark. For tests in which the active ingredients were not formulated, i.e. the technical active ingredient was used; a stock solution of the test compound was made. For example, a 100 ppm stock solution may be made by dissolving 4 milligrams of the test compound in 4 mL of acetone and adding the solution to 36 mL of an aqueous Triton X-100 solution (one drop of Triton X-100 dissolved in 100 mL of distilled water). Further dilutions can be made by adding distilled water containing 10% acetone and 0.25% of Triton X-100.

At the end of the 72 hour exposure period the numbers of dead and live insects were counted. Insects were classified as "dead" if they were off-color or brown and desiccated. Using the insect counts, the activity of the test chemical was expressed in percent control. Percent control is derived from the total number of dead insects (TD) compared to the total number of insects (TI) in the test:

$$\% \text{ Control} = \frac{TD}{TI} \times 100.$$

In tests against twospotted spider mites, the leaves of potted 3 to 4 inch tall pinto bean plants (*Phaseolus vulgaris*) were infested with about 50 to 75 adult twospotted spider mites by placing leaf cuttings from a twospotted spider mite colony host pinto bean plant on the upper surface of the test plant leaves. After about 1 hour the newly infested pinto bean leaves were dipped into the test solutions of the test formulations to provide application rates as high as 1000 ppm of the active ingredients. The test formulations were dissolved in, and diluted as necessary, with distilled water containing 10% acetone and 0.25% of a non-ionic detergent [an octylphenolpoly(ethyleneglycolether)$_x$, available from Roche Applied Science as Triton X-100] to the proper concentrations. The treated plants were transferred to a hood where they were kept until the leaves had dried. Once dry, the potted plants were placed into a tray containing at least one inch of water. The plants were spaced far enough apart to prevent the mites from moving between plants. The trays were held in a growth chamber for 96 hours at 25° C., 50% relative humidity and a photoperiod of 14 hours light/10 hours dark. For tests in which the active ingredients were not formulated, i.e. the technical active ingredient was used; a stock solution of the test compound was made. For example, a 100 ppm stock solution may be made by dissolving 4 milligrams of the test compound in 4 mL of acetone and adding the solution to 36 mL of an aqueous Triton X-100 solution (one drop of Triton X-100 dissolved in 100 mL of distilled water). Further dilutions can be made by adding distilled water containing 10% acetone and 0.25% of Triton X-100.

At the end of the 96 hour exposure period the numbers of dead and live insects were counted. Insects were classified as "dead" if they failed to show movement when probed. Using the insect counts, the activity of the test chemical was expressed in percent control. Percent control is derived from the total number of dead insects (TD) compared to the total number of insects (TI) in the test:

$$\% \text{ Control} = \frac{TD}{TI} \times 100.$$

Tobacco budworm insecticidal activity data at selected rates of application from this test are provided in Table 2. Adult Colorado potato beetle insecticidal activity data at selected rates of application from this test are provided in Table 3. Tables 2 and 3 also contain insecticidal results from individually tested formulations of bifenthrin (Capture 2EC®, available from FMC Corporation), and zeta-cypermethrin (Mustang Max 0.8EC®, available from FMC Corporation) as well as the control test results. For all cases reported in Tables 2 and 3, the test insecticide formulation comprised, % by weight of all components in the total formulation and (grams): 15.00% (19.45 grams) bifenthrin/zeta-cypermethrin (ratio of bifenthritheta-cypermethrin provided in the table), 7.00% (5.60 grams) of the surfactant blend, 25.00% (20.00 grams) of Sunspray 6N, 52.90% (42.32 grams) of aromatic 200, and 0.10% (0.08 gram) of acetic acid. The surfactant blend comprised 3.15% (2.52 grams) of Agnique ABS70AE, 0.35% (0.28 gram) of Agnique PEG 400 MO, 1.05% (0.84 gram) of Agnique CSO-36, and 2.45% (1.96 grams) of Agnique CSO-25. The bold numbers indicate that a beneficial insecticidal effect was observed when compared to the individual compounds.

TABLE 2

Tobacco Budworm (*Heliothis virescens* [Fabricius]) Insecticidal Activity of Bifenthrin and zeta-Cypermethrin (prepared by the process disclosed in U.S. Pat. No. 4,997,970)

| Treatment | Bifenthrin/zeta-Cypermethrin Ratio | Concentration Bifenthrin (ppm) | Concentration zeta-Cypermethrin (ppm) | Total Concentration (ppm) | Percent Mortality |
|---|---|---|---|---|---|
| Capture 2EC ® | 1/0 | 10.0 | 0 | 10.0 | 100 |
| Capture 2EC ® | 1/0 | 5.4 | 0 | 5.4 | 95 |
| Capture 2EC ® | 1/0 | 3.0 | 0 | 3.0 | 35 |
| Capture 2EC ® | 1/0 | 1.0 | 0 | 1.0 | 20 |
| Mustang Max 0.8EC ® | 0/1 | 0 | 10.0 | 10.0 | 90 |
| Mustang Max 0.8EC ® | 0/1 | 0 | 5.4 | 5.4 | 65 |
| Mustang Max 0.8EC ® | 0/1 | 0 | 3.0 | 3.0 | 40 |
| Mustang Max 0.8EC ® | 0/1 | 0 | 1.0 | 1.0 | 30 |
| Bifen/zeta | 2/1 | 6.7 | 3.3 | 10.0 | 95 |
| Bifen/zeta | 2/1 | 3.6 | 1.8 | 5.4 | 90 |
| Bifen/zeta | 2/1 | 2.0 | 1.0 | 3.0 | 80 |
| Bifen/zeta | 2/1 | 0.7 | 0.3 | 1.0 | 55 |
| Bifen/zeta | 1/1 | 5.0 | 5.0 | 10.0 | 90 |
| Bifen/zeta | 1/1 | 2.7 | 2.7 | 5.4 | 85 |
| Bifen/zeta | 1/1 | 1.5 | 1.5 | 3.0 | 70 |
| Bifen/zeta | 1/1 | .05 | .05 | 1.0 | 40 |
| Bifen/zeta | 1/2 | 3.3 | 6.7 | 10.0 | 100 |
| Bifen/zeta | 1/2 | 1.8 | 3.6 | 5.4 | 90 |
| Bifen/zeta | 1/2 | 1.0 | 2.0 | 3.0 | 75 |
| Bifen/zeta | 1/2 | 0.3 | 0.7 | 1.0 | 35 |
| Bifen/zeta | 1/3 | 2.5 | 7.5 | 10.0 | 90 |
| Bifen/zeta | 1/3 | 1.4 | 4.1 | 5.4 | 79 |
| Bifen/zeta | 1/3 | 0.8 | 2.3 | 3.0 | 85 |
| Bifen/zeta | 1/3 | 0.3 | 0.8 | 1.0 | 65 |
| Bifen/zeta | 1/4 | 2.0 | 8.0 | 10.0 | 100 |
| Bifen/zeta | 1/4 | 1.1 | 4.3 | 5.4 | 95 |
| Bifen/zeta | 1/4 | 0.6 | 2.4 | 3.0 | 85 |
| Bifen/zeta | 1/4 | 0.2 | 0.8 | 1.0 | 56 |
| Control | — | 0 | 0 | 0 | 0 |

As set forth in Table 2, test formulations of bifenthrin and zeta-cypermethrin at total concentrations of 3.0 ppm and lower provided better control of the tobacco budworm when compared to the individually tested formulations of bifenthrin (Capture 2EC®, available from FMC Corporation), and zeta-cypermethrin (Mustang Max 0.8EC®, available from FMC Corporation). One skilled in the art would expect the mixtures of bifenthrin and zeta-cypermethrin, at lower than normal use rates, to exhibit equivalent insecticidal activity to that of the individual insecticidal compounds. At rates of 3.0 ppm and lower, the novel formulated mixture exhibited up to twice the insecticidal activity of the insecticidal compounds at those rates and is within the insecticidal activity of the commercially suggested rates of 5.4 ppm and 10.0 ppm.

TABLE 3

Adult Colorado potato beetle (*Leptinotarsa decemlineata* [Say]) Insecticidal Activity of Bifenthrin and zeta-Cypermethrin (prepared by the process disclosed in U.S. Pat. No. 4,997,970)

| Treatment | Bifenthrin/zeta-Cypermethrin Ratio | Concentration Bifenthrin (ppm) | Concentration zeta-Cypermethrin (ppm) | Total Concentration (ppm) | Percent Mortality |
|---|---|---|---|---|---|
| Capture 2EC ® | 1/0 | 10.0 | 0 | 10.0 | 35 |
| Mustang Max 0.8EC ® | 0/1 | 0 | 10.0 | 10.0 | 30 |
| Bifen/zeta | 2/1 | 6.7 | 3.3 | 10.0 | 90 |
| Bifen/zeta | 1/1 | 5.0 | 5.0 | 10.0 | 95 |
| Bifen/zeta | 1/2 | 3.3 | 6.7 | 10.0 | 70 |
| Bifen/zeta | 1/3 | 2.5 | 7.5 | 10.0 | 70 |
| Bifen/zeta | 1/4 | 2.0 | 8.0 | 10.0 | 65 |
| Control | — | 0 | 0 | 0 | 0 |

As set forth in Table 3, test formulations of bifenthrin and zeta-cypermethrin, at a total concentration of 10.0 ppm, provided better control of the Colorado potato beetle when compared to the individually tested formulations of bifenthrin (Capture 2EC®, available from FMC Corporation) and zeta-cypermethrin (Mustang Max 0.8EC®, available from FMC Corporation). One skilled in the art would expect the mixtures of bifenthrin and zeta-cypermethrin to exhibit insecticidal activity equivalent to that of the individual insecticidal compounds. At the tested rate of 10.0 ppm, the insecticidal activity of the novel formulated mixture exhibited two to three times the insecticidal activity of the individual insecticidal compounds.

Adult Colorado potato beetle insecticidal activity data at selected rates of application in which the technical active ingredients were dissolved as described above are provided in Table 4. The bold and italicized numbers indicate that a beneficial insecticidal effect was observed when compared to the individual compounds.

TABLE 4

Adult Colorado potato beetle (*Leptinotarsa decemlineata* [Say]) Insecticidal Activity of Bifenthrin and Cyano-pyrethroids

| Cyano Pyrethroid | Rate of Application (ppm) | % Mortality Adult Colorado Potato Beetle bifenthrin Rate of Application (ppm) | | | |
|---|---|---|---|---|---|
| | | 0 | 0.3 | 1.0 | 3.0 |
| cyfluthrin | 0 | 0 | 0 | 0 | 80 |
| | 0.3 | 10 | 0 | 10 | 60 |
| | 1.0 | 70 | 70 | 70 | *90* |
| | 3.0 | 80 | 80 | *100* | *100* |
| | 10.0 | 100 | 100 | 100 | 100 |
| lambda-cyhalothrin | 0 | 0 | 0 | 0 | 80 |
| | 0.3 | 30 | *50* | *70* | *100* |
| | 1.0 | 100 | 90 | 100 | 100 |
| | 3.0 | 100 | 100 | 100 | 100 |
| | 10.0 | 100 | 100 | 100 | 100 |
| delta-methrin | 0 | 0 | 0 | 0 | 10 |
| | 0.3 | 0 | 0 | 0 | 0 |
| | 1.0 | 30 | *60* | *60* | 30 |
| | 3.0 | 90 | *100* | 90 | 80 |
| | 10.0 | 100 | 100 | 100 | 100 |
| esfenvalerate[a] | 0 | 0 | 0 | 10 | 70 |
| | 0.3 | 0 | 0 | *20* | 40 |
| | 1.0 | 0 | 0 | 10 | 35 |
| | 3.0 | 5 | *60* | *55* | 45 |
| | 10.0 | 95 | 85 | *100* | 95 |
| alpha-cypermethrin | 0 | 0 | 0 | 0 | 10 |
| | 0.3 | 30 | 0 | 0 | 20 |
| | 1.0 | 70 | 30 | 10 | *100* |
| | 3.0 | 100 | 70 | NT | 100 |
| | 10.0 | 100 | 90 | 100 | 100 |

[a] % mortality for esfenvalerate and bifenthrin is the average of two tests.

Corn earworm insecticidal activity data at selected rates of application in which the technical active ingredients were dissolved as described above are provided in Table 5. The bold and italicized numbers indicate that a beneficial insecticidal effect was observed when compared to the individual compounds.

TABLE 5

Corn Earworm (*Heliothis zea* [Boddie]) Insecticidal Activity of Bifenthrin and Cyano-pyrethroids

| Cyano Pyrethroid | Rate of Application (ppm) | % Mortality Corn Earworm bifenthrin Rate of Application (ppm) | | | |
|---|---|---|---|---|---|
| | | 0.0 | 0.1 | 0.3 | 1.0 |
| cyfluthrin | 0 | 6 | NT | 13 | 100 |
| | 0.3 | 13 | NT | *31* | 63 |
| | 1.0 | 69 | NT | *88* | 100 |
| | 3.0 | 100 | NT | 100 | 100 |
| | 10.0 | 100 | NT | 100 | 100 |
| lambda-cyhalothrin | 0 | 0 | 6 | 13 | 75 |
| | 0.3 | 6 | 0 | 13 | 75 |
| | 1.0 | 31 | 19 | *56* | *100* |
| | 3.0 | 56 | *75* | *94* | *100* |
| | 10.0 | 100 | 94 | 100 | 100 |
| delta-methrin | 0 | 0 | 6 | 13 | 75 |
| | 0.3 | 6 | *13* | *38* | *94* |
| | 1.0 | 50 | *56* | *75* | *100* |
| | 3.0 | 94 | *100* | *100* | *100* |
| | 10.0 | 100 | 100 | 100 | 100 |
| esfenvalerate | 0 | 0 | 6 | 13 | 75 |
| | 0.3 | 0 | 0 | 0 | *82* |
| | 1.0 | 0 | *13* | 13 | *67* |
| | 3.0 | 13 | *19* | *62* | *100* |
| | 10.0 | 50 | *88* | 75 | *100* |
| alpha-cypermethrin | 0 | 0 | 6 | 25 | 63 |
| | 0.3 | 6 | *12* | *75* | *100* |
| | 1.0 | 63 | 38 | 63 | *100* |
| | 3.0 | 100 | 94 | 100 | 100 |
| | 10.0 | 100 | 100 | 100 | 100 |

Cotton aphid insecticidal activity data at selected rates of application in which the technical active ingredients were dissolved as described above are provided in Table 6. The bold and italicized numbers indicate that a beneficial insecticidal effect was observed when compared to the individual compounds.

TABLE 6

Cotton Aphid (*Aphis gossypii* [Glover]) Insecticidal Activity of Bifenthrin and Cyano-pyrethroids

| Cyano Pyrethroid | Rate of Application (ppm) | % Mortality Cotton Aphid bifenthrin Rate of Appleation (ppm) | | | |
|---|---|---|---|---|---|
| | | 0 | 30.0 | 100.0 | 200.0 |
| cyfluthrin | 0 | 4 | 15 | 30 | NT* |
| | 10.0 | 4 | 8 | *58* | NT |
| | 30.0 | 6 | 13 | *78* | NT |
| | 100.0 | 9 | 3 | *56* | NT |
| lambda-cyhalothrin | 0 | 4 | 15 | 30 | NT |
| | 10.0 | 11 | *22* | *53* | NT |
| | 30.0 | 11 | 15 | *71* | NT |
| | 100.0 | 10 | *45* | *80* | NT |
| delta-methrin | 0 | 2 | 35 | 88 | 100 |
| | 30.0 | 7 | 11 | 46 | 55 |
| | 100.0 | 8 | 33 | 63 | 90 |
| | 200.0 | 19 | *42* | 63 | 100 |
| Esfenvalerate[a] | 0 | 5 | 34 | 94 | 100 |
| | 30.0 | 38 | *41* | 93 | 91 |
| | 100.0 | 14 | *45* | 92 | 100 |
| | 200.0 | 15 | 32 | *97* | 93 |
| alpha-cypermethrin | 0 | 6 | 17 | 100 | 100 |
| | 30.0 | 7 | 16 | 70 | 69 |
| | 100.0 | 3 | 10 | 43 | 100 |
| | 200.0 | 7 | *19* | 50 | 92 |

*NT = Not Tested
[a] % mortality for esfenvalerate and bifenthrin is the average of two tests.

Twospotted spider miticidal activity data at selected rates of application in which the technical active ingredients were dissolved as described above are provided in Table 7. The bold and italicized numbers indicate that a beneficial insecticidal effect was observed when compared to the individual compounds.

TABLE 7

Twospotted Spider Mite (*Tetranychus urticae* [Koch]) Insecticidal Activity of Bifenthrin and Cyano-pyrethroids

| Cyano Pyrethroid | Rate of Application (ppm) | % Mortality Twospotted Spider Mite bifenthrin Rate of Application (ppm) | | | | |
|---|---|---|---|---|---|---|
| | | 0 | 10.0 | 30.0 | 60.0 | 100.0 |
| cyfluthrin | 0 | 1 | 20 | 66 | 68 | 75 |
| | 10.0 | 14 | 5 | 24 | *79* | 57 |
| | 30.0 | 17 | 4 | 46 | 66 | *97* |
| | 60.0 | 23 | 10 | *100* | 95 | *100* |
| | 100.0 | 11 | 96 | 42 | *100* | *91* |
| lambda-cyhalothrin | 0 | 1 | 20 | 66 | 68 | 75 |
| | 10.0 | 16 | 5 | *83* | *96* | *84* |
| | 30.0 | 19 | *20* | *95* | *85* | *94* |
| | 60.0 | 55 | *68* | *100* | *96* | *96* |
| | 100.0 | 39 | *78* | *93* | *95* | *97* |
| delta-methrin | 0 | 12 | 9 | 100 | NT* | 90 |
| | 10.0 | 3 | *95* | 100 | NT | *100* |
| | 30.0 | 83 | *100* | 100 | NT | *100* |
| | 100.0 | 26 | *100* | 97 | NT | *100* |
| | 200.0 | 16 | *94* | 100 | NT | *100* |
| esfenvalerate | 0 | 12 | 9 | 100 | NT | 90 |
| | 10.0 | 21 | *35* | 100 | NT | *97* |
| | 30.0 | 25 | 18 | 98 | NT | *99* |
| | 100.0 | 71 | 60 | 95 | NT | *100* |
| | 200.0 | 91 | *98* | 94 | NT | *98* |
| alpha-cypermethrin | 0 | 4 | 16 | 69 | NT | 100 |
| | 10.0 | 8 | *23* | *80* | NT | 95 |
| | 30.0 | 8 | *31* | 87 | NT | 100 |
| | 100.0 | 16 | *57* | *94* | NT | 91 |
| | 200.0 | 32 | *46* | *94* | NT | 90 |

*NT = Not Tested

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. An insecticidal composition comprising bifenthrin and a cyano-pyrethroid selected from the group consisting of acrinathrin, cycloprothrin, deltamethrin, tralomethrin, fenvalerate, cyfluthrin, beta-cyfluthrin, flucythrinate, alpha-cypermethrin, beta-cypermethrin, theta-cypermethrin, zeta-cypermethrin, cyphenothrin, cyhalothrin, lambda-cyhalothrin, esfenvalerate, fluvalinate and fenpropathrin, wherein the composition has a ratio of bifenthrin:cyano-pyrethroid of from about 10:1 to about 1:100.

2. The insecticidal composition of claim 1 further comprising in admixture at least one agriculturally acceptable extender or adjuvant.

3. The insecticidal composition of claim 2 wherein the cyano-pyrethroid is at least one selected from the group consisting of: deltamethrin; cyfluthrin; alpha-cypermethrin; zeta-cypermethrin; lambda-cyhalothrin; and esfenvalerate.

4. The insecticidal composition of claim 3 wherein the at least one cyano-pyrethroid is zeta-cypermethrin and wherein the composition comprises bifenthrin and zeta-cypermethrin in a ratio of from about 2:1 to about 1:4 (bifenthrin:zeta-cypermethrin), and wherein bifenthrin is present in the composition at a concentration of less than or equal to about 6.7 ppm.

5. The insecticidal composition of claim 4 wherein the zeta-cypermethrin is (R,S)-α-cyano-3-phenoxybenzyl-(1RS)-cis-trans-3-(2,2-dichlorovinyl)-2,2-dimethylcyclopropanecarboxylate which has been enriched in the 1R-cis-S and 1R-trans-S isomers by the reaction of a 55% cis/45% trans mixture of cypermethrin with a catalytic amount of tricaprylylammonium chloride and sodium carbonate in n-heptane.

6. A method for controlling unwanted insects comprising the step of applying a composition of claim 1 to a locus where insects are present or are expected to be present.

7. The insecticidal composition of claim 3 wherein the at least one cyano-pyrethroid is deltamethrin and wherein the composition comprises bifenthrin and deltamethrin in a ratio of from about 1:1 to about 1:20 (bifenthrin:deltamethrin).

8. The insecticidal composition of claim 3 wherein the at least one cyano-pyrethroid is cyfluthrin and wherein the composition comprises bifenthrin and cyfluthrin in a ratio of from about 10:1 to about 1:3 (bifenthrin:cyfluthrin).

9. The insecticidal composition of claim 3 wherein the at least one cyano-pyrethroid is alpha-cypermethrin and wherein the composition comprises bifenthrin and alpha-cypermethrin in a ratio of from about 3:1 to about 1:10 (bifenthrin:alpha-cypermethrin).

10. The insecticidal composition of claim 3 wherein the at least one cyano-pyrethroid is lambda-cyhalothrin and wherein the composition comprises bifenthrin and lambda-cyhalothrin in a ratio of from about 10:1 to about 1:10 (bifenthrin:lambda-cyhalothrin).

11. The insecticidal composition of claim 3 wherein the at least one cyano-pyrethroid is esfenvalerate and wherein the composition comprises bifenthrin and esfenvalerate in a ratio of from about 3:1 to about 1:100 (bifenthrin:esfenvalerate).

* * * * *